(12) United States Patent
Hickey et al.

(10) Patent No.: US 8,771,999 B2
(45) Date of Patent: Jul. 8, 2014

(54) LOW ENERGY, HIGH SUBSTRATE EFFICIENCY, ANAEROBIC, DEEP, BUBBLE COLUMN FERMENTATION PROCESSES

(75) Inventors: Robert Hickey, Okemos, MI (US); Richard E. Tobey, St. Charles, IL (US)

(73) Assignee: Coskata, Inc., Warrenville, IL (US)

( * ) Notice: Subject to any disclaimer, the term of this patent is extended or adjusted under 35 U.S.C. 154(b) by 129 days.

(21) Appl. No.: 13/243,062

(22) Filed: Sep. 23, 2011

(65) Prior Publication Data

US 2013/0078688 A1    Mar. 28, 2013

(51) Int. Cl.
*C12P 7/00* (2006.01)
*C12P 7/06* (2006.01)
*C12P 7/14* (2006.01)
*C12P 7/54* (2006.01)

(52) U.S. Cl.
USPC .......................... 435/132; 435/140; 435/161

(58) Field of Classification Search
None
See application file for complete search history.

(56) References Cited

U.S. PATENT DOCUMENTS

| | | | |
|---|---|---|---|
| 4,162,970 | A | 7/1979 | Zlokarnik et al. |
| 4,426,450 | A | 1/1984 | Donofrio |
| 6,193,220 | B1 | 2/2001 | Kelly |
| 7,285,402 | B2 | 10/2007 | Gaddy et al. |
| 7,704,723 | B2 | 4/2010 | Huhnke et al. |
| 2003/0211585 | A1 | 11/2003 | Gaddy et al. |
| 2008/0305539 | A1 | 12/2008 | Hickey et al. |
| 2009/0215139 | A1 | 8/2009 | Datta et al. |
| 2011/0059499 | A1 | 3/2011 | Simpson et al. |

OTHER PUBLICATIONS

Datar et al. "Fermentation of Biomass-Generated Producer Gas to Ethanol". Biotechnology and Bioengineering. 2004, vol. 86, No. 5, 587-594.*

Kantarci et al. "Bubble column reactors". Process Biochemistry 40 (2005) 2263-2283.*

Munasinghe, et al., Biomass-derived Syngas Fermentation in Biofuels: Opportunities and Challenges, Biosource Technology, 101 (2010) 5013-5022.

Munasinghe, et al., Syngas Fermentation to Biofuel: Evaluation of Carbon Monoxide Mass Transfer Coefficient (kLa) in Different Reactor Configurations, Biotechol. Prog., 2010.

Bredwell, et al., in Reactor Design Issues for Synthesis-Gas Fermentations, Biotechnol. Prog., 15 (1999) 834-844.

Xu, et al., The effects of syngas impurities on syngas fermentation to liquid fuels, Biomass and Bioenergy, 35, (2011), 2690-2696.

Krishna, et al., Influence of alcohol addition on gas hold-up in bubble columns: development of a scale up model, Int. Comm. Heat Mass Transfer, 27 No. 4, (2000) 465-472.

Wilkins, et al., Microbial productoin of ethanol from carbon monoxide, Current Opinion in Biotechnology, 22 (2011), 326-330.

Ahmed, et al., Fermentation of Biomass-Generated Synthesis Gas: Effects of Nitric Oxide, Biotechnology and Bioengineering, 97, No. 5, (2007), 1080-1086.

Abubackar, et al., Biological conversion of carbon monoxide: rich syngas or waste gas to bioethanol, Biofuels, Bioproducts & Biorefining, 5 (2011), 93-114.

* cited by examiner

*Primary Examiner* — Vera Afremova
(74) *Attorney, Agent, or Firm* — Cardinal Law Group LLC

(57) ABSTRACT

Bioconversion processes are disclosed that enable high conversion efficiencies of gas substrate containing both carbon monoxide and hydrogen to oxygenated organic compounds via the carbon monoxide and hydrogen pathways using anaerobic, deep, bubble column fermentation in a cost effective manner. The high conversion efficiency processes of this invention comprise the combination of using at least two deep, bubble column reactors in flow series and using certain feed gas compositions and microbubbles while avoiding carbon monoxide inhibition.

20 Claims, 3 Drawing Sheets

LOW ENERGY, HIGH SUBSTRATE EFFICIENCY, ANAEROBIC, DEEP, BUBBLE COLUMN FERMENTATION PROCESSES

FIELD OF THE INVENTION

This invention pertains to processes for the low energy, anaerobic bioconversion of hydrogen and carbon monoxide in a gaseous substrate stream to oxygenated organic compounds such as ethanol by contact with microorganisms in a deep, bubble column fermentation system with high conversion efficiency of both hydrogen and carbon monoxide.

BACKGROUND

Anaerobic fermentations of hydrogen and carbon monoxide involve the contact of the substrate gas in a liquid aqueous menstruum with microorganisms capable of generating oxygenated organic compounds such as ethanol, acetic acid, propanol and n-butanol. The production of these oxygenated organic compounds requires significant amounts of hydrogen and carbon monoxide. For instance, the theoretical equations for the conversion of carbon monoxide and hydrogen to ethanol are:

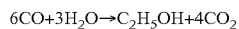

$$6CO + 3H_2O \rightarrow C_2H_5OH + 4CO_2$$

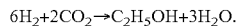

$$6H_2 + 2CO_2 \rightarrow C_2H_5OH + 3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Typically the substrate gas for carbon monoxide and hydrogen conversions is, or is derived from, a synthesis gas (syngas) from the gasification of carbonaceous materials, from the reforming of natural gas and/or biogas from anaerobic digestion or from off-gas streams of various industrial methods. The gas substrate contains carbon monoxide, hydrogen, and carbon dioxide and usually contains other components such as water vapor, nitrogen, methane, ammonia, hydrogen sulfide and the like. (For purposes herein, all gas compositions are reported on a dry basis unless otherwise stated or clear from the context.)

These substrate gases are typically more expensive than equivalent heat content amounts of fossil fuels. Hence, a desire exists to use these gases efficiently to make higher value products. The financial viability of any conversion process, especially to commodity chemicals such as ethanol and acetic acid, will be dependent upon capital costs, the efficiency of conversion of the carbon monoxide and hydrogen to the sought products and the energy costs to effect the conversion.

Syngas fermentation processes suffer from the poor solubility of the gas substrate, i.e., carbon dioxide and hydrogen, in the liquid phase of the aqueous menstruum where the biological processes occur. Munasinghe, et al., in *Biomass-derived Syngas Fermentation in Biofuels: Opportunities and Challenges, Biosource Technology*, 101 (2010) 5013-5022, summarize volumetric mass transfer coefficients to fermentation media that are reported in the literature for syngas and carbon monoxide in various reactor configurations and hydrodynamic conditions. A number of conditions can enhance the mass transfer of syngas to the liquid phase. For instance, increasing the interfacial area between the gas feed and the liquid phase can improve mass transfer rates.

Numerous processes have been disclosed for the conversion of carbon monoxide and hydrogen to oxygenated compounds. One such process suspends the microorganisms for the conversion in an aqueous menstruum contained in a stirred tank reactor such as by using a motor driven impeller. Stirred tank fermentation reactors provide many advantages. For stirred tank reactors, increasing the agitation of the impeller improves mass transfer as smaller bubble sizes are obtained. Also, the stirring action not only distributes the gas phase in the aqueous menstruum but also the duration of the contact between the phases can be controlled. Another very significant benefit is that the composition within the stirred tank can be relatively uniform. For instance, Munasignhe, et al., in a later published paper, *Syngas Fermentation to Biofuel: Evaluation of Carbon Monoxide Mass Transfer Coefficient ($k_La$) in Different Reactor Configurations, Biotechol. Prog.*, 2010, Vol. 26, No. 6, pp 1616-1621, combine a sparger (0.5 millimeter diameter pores) with mechanical mixing at various rotational rates to provide enhanced mass transfer. This uniformity enables good control of the fermentation process during steady-state operation. This is of particular advantage in the anaerobic conversion of carbon monoxide and hydrogen to oxygenated compounds where two conversion pathways exist. Hence the carbon dioxide generated from the conversion of carbon monoxide is proximate in location to the hydrogen consumption pathway that consumes carbon dioxide. The uniformity further facilitates the addition of fresh gas substrate. The problems with stirred tank reactors are capital costs, the significant amount of energy consumed in the needed mixing and agitation, and the need for plural stages to achieve high conversion of substrate.

Another type of fermentation apparatus is a bubble column reactor wherein the substrate gas is introduced at the bottom of the vessel and bubbles through the aqueous menstruum ("bubble reactor"). See Munasinghe, et al., in *Biomass-derived Syngas Fermentation in Biofuels: Opportunities and Challenges, Biosource Technology*, 101 (2010) 5013-5022. In order to achieve sought mass transfer from the gas to liquid phases, workers have provided the gas feed to bubble columns in the form of microbubbles. Microbubble spargers were used to generate microbubbles. The authors report that in one study, the mass transfer obtained for a bubble column reactor was higher than that for a stirred tank reactor mainly due to the higher interfacial surface area obtained because of the smaller bubble size generated by the sparger used with the bubble column reactor.

Bredwell, et al., in *Reactor Design Issues for Synthesis-Gas Fermentations, Biotechnol. Prog.*, 15 (1999) 834-844, assessed various types of reactors including bubble columns and stirred reactors. The authors disclose using microbubble sparging with mechanical agitation. At page 839 they state:

"When microbubble sparging is used, only enough power must be applied to the reactor to provide adequate liquid mixing. Thus axial flow impellers designed to have low shear and a high pumping capacity would be suitable when microbubbles are used in stirred tanks."

They conclude by stating:

"An improved ability to predict and control coalescence rates is needed to rationally design commercial-scale bioreactors that employ microbubble sparging." (p. 841)

Advantageously, commercial-scale bubble column reactors are relatively simple in design and construction and require relatively little energy to operate. However, microbubble spargers, especially for very small microbubbles, use significant amounts of energy and are prone to fouling. Accordingly, other means for generating microbubbles such as injectors using a motive fluid that are not prone to fouling, are preferred. Co-pending U.S. patent application Ser. No. 12/826,991, filed on Jun. 30, 2010, herein incorporated by reference in its entirety, discloses the use of injectors to supply gas feed to an anaerobic fermentation in a deep reactor to make a liquid product such as ethanol wherein the presence of the liquid product enables the injector to produce a dispersion of microbubbles.

For deep, bubble column reactors, the height of the aqueous menstruum is a primary determinant of the gas/liquid contact time. This height also is a determinant of the static head at the bottom portion of the reactor. Higher pressures result in smaller bubble sizes and higher partial pressures both of which enhance mass transfer efficiency and gas substrate conversion efficiency in the fermentation reactor. Thus, on a commercial scale, deep, bubble column reactors would have to have a depth of at least about 10, preferably at least about 15, meters and use microbubbles of gas feed in order to achieve viable conversion efficiencies. However, without the mechanical stifling of a stirred tank reactor, the compositions of the gas phase and liquid phase in a deep, bubble column reactor change over the depth of the vessel due to bioconversions and changes in gas solubility in the aqueous phase.

In their earlier review article, Munasignhe, et al., report that the gas-liquid mass transfer is the major resistance for gaseous substrate diffusion. The authors state at page 5017:
"High pressure operation improves the solubility of the gas in the aqueous phase. However, at higher concentrations of gaseous substrates, especially CO, anaerobic microorganisms are inhibited."

Other workers have understood that the presence of excess carbon monoxide can adversely affect the microorganisms and their performance. See paragraphs 0075 through 0077 and 0085 though 0086 of United States published patent application No. 20030211585 (Gaddy, et al.) disclosing a continuously stirred tank bioreactor for the production of ethanol from microbial fermentation. At paragraph 0077, Gaddy, et al., state:
"The presence of excess CO unfortunately also results in poor $H_2$ conversion, which may not be economically favorable. The consequence of extended operation under substrate inhibition is poor $H_2$ uptake. This eventually causes cell lysis and necessary restarting of the reactor. Where this method has an unintended result of CO substrate inhibition (the presence of too much CO for the available cells) during the initial growth of the culture or thereafter, the gas feed rate and/or agitation rate is reduced until the substrate inhibition is relieved."

At paragraph 0085, Gaddy, et al., discuss supplying excess carbon monoxide and hydrogen. They state:
"A slight excess of CO and $H_2$ is achieved by attaining steady operation and then gradually increasing the gas feed rate and/or agitation rate (10% or less increments) until the CO and $H_2$ conversions just start to decline."

The gas feed is introduced at the bottom of a deep, bubble column reactor where the most favorable conditions for mass transfer of carbon monoxide from the gas to the liquid phase exist. Hence, to avoid carbon monoxide inhibition, operating parameters such as carbon monoxide mole fraction in the gas feed, gas feed supply rate and microbubble size must be controlled to assure that the carbon monoxide mass transfer rate does not become so great as to cause carbon monoxide inhibition. However, the conditions required to avoid carbon monoxide inhibition in a deep, bubble column reactor negatively affect the overall amount of carbon monoxide that can be transferred to the liquid phase, and thus the conversion efficiency to oxygenated organic compound.

This negative effect is exacerbated since the static pressure is reduced as the microbubbles pass upwardly, the partial pressure of carbon monoxide in the bubbles decreases and the surface area to volume of the microbubbles may decrease. Furthermore, the compositions of the gas and liquid phases change over the height of the aqueous menstruum, further negatively affecting mass transfer of hydrogen and carbon monoxide to the liquid phase. Carbon dioxide co-product is generated by the carbon monoxide pathway and the solubility of carbon dioxide in the aqueous menstruum is highly sensitive to pressure. Thus, at higher elevations of the aqueous menstruum, carbon dioxide can pass to the bubbles and reduce the mole fractions of hydrogen and carbon monoxide in the gas phase. The reduced mole fractions also reduce the driving force for mass transfer of carbon monoxide and hydrogen to the liquid phase.

The net result is that conversion efficiencies, especially for hydrogen, in a deep, bubble column reactor are often low. Increasing the depth to provide a longer contact time provides ever diminishing benefits, increases the risk of carbon monoxide inhibition and thus is not a solution by itself to obtain sought high bioconversion efficiencies.

Recycling the off-gases from the top of a deep, bubble column reactor is possible as these gases contain unreacted carbon monoxide and hydrogen. However, as the conversion efficiency of hydrogen and carbon monoxide increases, the off-gases have such a reduced concentration of hydrogen and carbon monoxide, that recycling is impractical and may lead to inefficiencies due to a dilution of the mole fractions of carbon monoxide and hydrogen in the gas feed to the aqueous menstruum.

Processes are therefore sought to capture the benefits provided by a bubble column fermentation system and to be able to enhance the conversion of hydrogen and carbon monoxide without undue risk of carbon monoxide inhibition.

SUMMARY OF THE INVENTION

By this invention bioconversion processes are provided that enable the use of deep, bubble column reactors to achieve high conversions of carbon monoxide and hydrogen to oxygenated organic compound by anaerobic fermentation while minimizing the risk of carbon monoxide inhibition. Advantageous embodiments of this invention are commercially attractive from the stand points of capital and operating costs as well as the high molar conversion efficiencies often in excess of 80 or 85 percent of total carbon monoxide and hydrogen contained in the gas feed.

The processes of this invention comprise the combination of (i) using at least two deep, bubble column reactors in flow series; (ii) using certain feed gas compositions; (iii) introducing the feed gas by injection with a motive liquid to produce microbubbles; and (iv) limiting the degree of conversion of carbon monoxide in the upstream reactor. For purposes of facilitating the reading of this disclosure, an upstream reactor of the flow series is herein designated as the "primary deep, bubble column reactor" or "primary reactor" and the following of which is herein designated as the "sequential reactor".

In further detail of the broad aspects of the processes of this invention for the bioconversion of a gas feed containing gas substrate comprising carbon monoxide, carbon dioxide and hydrogen in an aqueous menstruum containing microorganisms suitable for converting said gas substrate to oxygenated organic compound comprise:
  a. providing the aqueous menstruum in at least one primary deep, bubble column reactor to a height of at least 10 meters wherein the gas feed is injected in a bottom portion of the reactor and wherein the pressure of the aqueous menstruum is at least about 100 kPa gauge, preferably at least about 150 kPa gauge, often in the range of about 150 to 500 kPa gauge, at said portion, b. continuously supplying to the bottom portion of said reactor said gas feed as microbubbles by injection using a motive liquid, said gas feed:
   (i) containing at least about 2, preferably at least about 5, say, 5 to 15, mole percent nitrogen,
   (ii) containing at least about 5, preferably at least about 10, say, about 10 to 60, mole percent carbon dioxide,
   (iii) having a mole ratio of hydrogen to carbon monoxide between about 1:6 to 6:1, preferably between about 1:4 to 2:1, say, about 1:2 to 2:1, and
   (iv) having mole fractions of carbon dioxide and nitrogen sufficient to provide a carbon monoxide partial pressure at the point of injection of less than about 80 kPa, say, between about 20 and 75 kPa, and preferably between about 25 and 70 kPa;

c. converting less than about 80, preferably less than about 75, say about 40 to 75, often 60 to 75, percent of the carbon monoxide in the gas feed supplied to the primary deep, bubble column reactor to oxygenated organic compound and providing an off-gas above the aqueous menstruum;

d. optionally removing at least a portion of the carbon dioxide from the aqueous menstruum in the primary deep, bubble column reactor or from at least a portion of the off-gas from the primary deep, bubble column reactor;

e. continuously supplying as microbubbles at least a portion of the off-gas from the primary deep, bubble column reactor by injection using a motive liquid to a lower portion of at least one sequential deep, bubble column reactor containing aqueous menstruum in which said off-gas passes upwardly through the aqueous menstruum wherein the off-gas has a mole fraction of nitrogen sufficient to avoid a mass transfer of carbon monoxide to the aqueous menstruum that results in carbon monoxide inhibition; and f. converting sufficient hydrogen and carbon monoxide in the sequential deep, bubble column reactor to oxygenated organic compound such that at least about 75, preferably at least about 80, and often about 85 to 95, percent of the total moles of carbon monoxide and hydrogen in the gas feed to the primary deep, bubble column reactor is converted to oxygenated compound.

The sequential, deep, bubble column reactor advantageously converts at least about 40, preferably at least about 50, say, between about 50 and 80, percent of the total moles of hydrogen and carbon monoxide in its gas feed.

Both the primary and sequential reactors used in the processes of this invention have a depth of at least about 10 meters, and often between about 15 and 30 meters. This depth provides sufficient time for contact with the menstruum to achieve the sought transfer of carbon monoxide and hydrogen to the aqueous menstruum and thus enable the sought conversion of carbon monoxide and hydrogen. The depth of the aqueous menstruum also facilitates small bubble sizes of gas feed and enhances transfer of the gases into the liquid aqueous menstruum, all of which are important to the goal of achieving a combination of high conversion efficiencies and advantaged capital and energy costs as compared to stirred tank reactor systems.

The extent of conversion of carbon monoxide in the primary reactor can be affected by a number of parameters. For instance, in addition to the height of the aqueous menstruum which increases the contact time for transfer of carbon monoxide from the gas to going into solution in the liquid phase, the mole fraction of carbon monoxide in the gas feed affects the rate of transfer of carbon monoxide to the liquid phase for bioconversion. Also, the size of the microbubbles can be changed. For a given volume of gas feed, a smaller microbubble size provides a greater interfacial surface area which increases mass transfer rates of carbon monoxide to the liquid phase. In accordance with the invention the gas feed is supplied by injectors that use a motive fluid containing oxygenated organic compound or other surface active agent. The injectors may be of any suitable design. Jet injectors, especially slot injectors, are generally preferred, particularly as greater aqueous menstruum heights are achieved in the start-up process. Slot injectors have a high turn down ratio with respect to the motive liquid flow rate per injector used while still providing good microbubble formation. In general, the average bubble diameter decreases as the rate of motive liquid flow is increased. By modulating the gas feed supply rates and the flow rates of the motive liquid, the size of the microbubbles can be controlled. Additionally, the modulation enables a microbubble size to be generated that results in a preferred, stable gas-in-water dispersion.

An objective in operating most commercial production facilities is to maximize conversion of feedstock. Advantageously, because the processes of this invention use two deep, bubble column reactors in flow sequence, achieving high production rates in accordance with the processes of this invention does not require that the primary reactor be operated with such high mass transfer rates of carbon monoxide to the liquid phase that undue risks of carbon monoxide inhibition exist.

Preferably at least a majority, and preferably at least about 60 percent of the carbon monoxide in the gas feed to the primary deep, bubble column reactor is bioconverted in the primary reactor. Often the fraction of the hydrogen that is bioconverted in the primary reactor is less than the fraction of carbon monoxide that is bioconverted. As the majority of the co-product carbon dioxide is generated in the primary reactor, the problem of carbon dioxide reducing the gas phase mole fraction of carbon monoxide and hydrogen as the microbubbles pass upwardly in the aqueous menstruum of the sequential reactor, is attenuated. Accordingly, the sequential reactor can more readily achieve high overall conversion of both carbon monoxide and hydrogen. Further, as the mole ratio of carbon monoxide to hydrogen in the feed to the subsequent reactor would be lower than that ratio in the gas feed to the primary reactor due to this preferential conversion of carbon monoxide, the risk of carbon monoxide inhibition can be further decreased in the sequential reactor.

Preferably at least a portion of the carbon dioxide is removed from one or both of the aqueous menstruum in the primary reactor and from the off-gas from the primary reactor. Most preferably, carbon dioxide is removed from the off-gas from the primary reactor. Often carbon dioxide comprises from about 10 to 70, say, 15 to 60, mole percent of the off-gas from the primary reactor where no removal of carbon dioxide from the aqueous menstruum occurs. Removal of carbon dioxide increases the mole fraction of carbon monoxide in the off-gas from the primary reactor, all else remaining the same. However, the presence of nitrogen provides a safeguard to protect the sequential reactor from inadvertent carbon monoxide inhibition in the event that conversion of carbon monoxide in the primary reactor is more or less than targeted and in the event that the removal of carbon dioxide is more or less than targeted.

At least a portion, preferably at least about 90 volume percent, and most preferably essentially all, of the off-gas (not including any carbon dioxide removed) from a primary reactor is passed to a sequential reactor. Where a plurality of primary reactors is used, the off-gas from two or more primary reactors may be combined for passing to a sequential reactor. Also, the gas feed to the sequential reactor may include gas from other sources including fresh feed and recycle gas from the sequential or a further, subsequent reactor.

DETAILED DISCUSSION

Definitions

Figure 1:
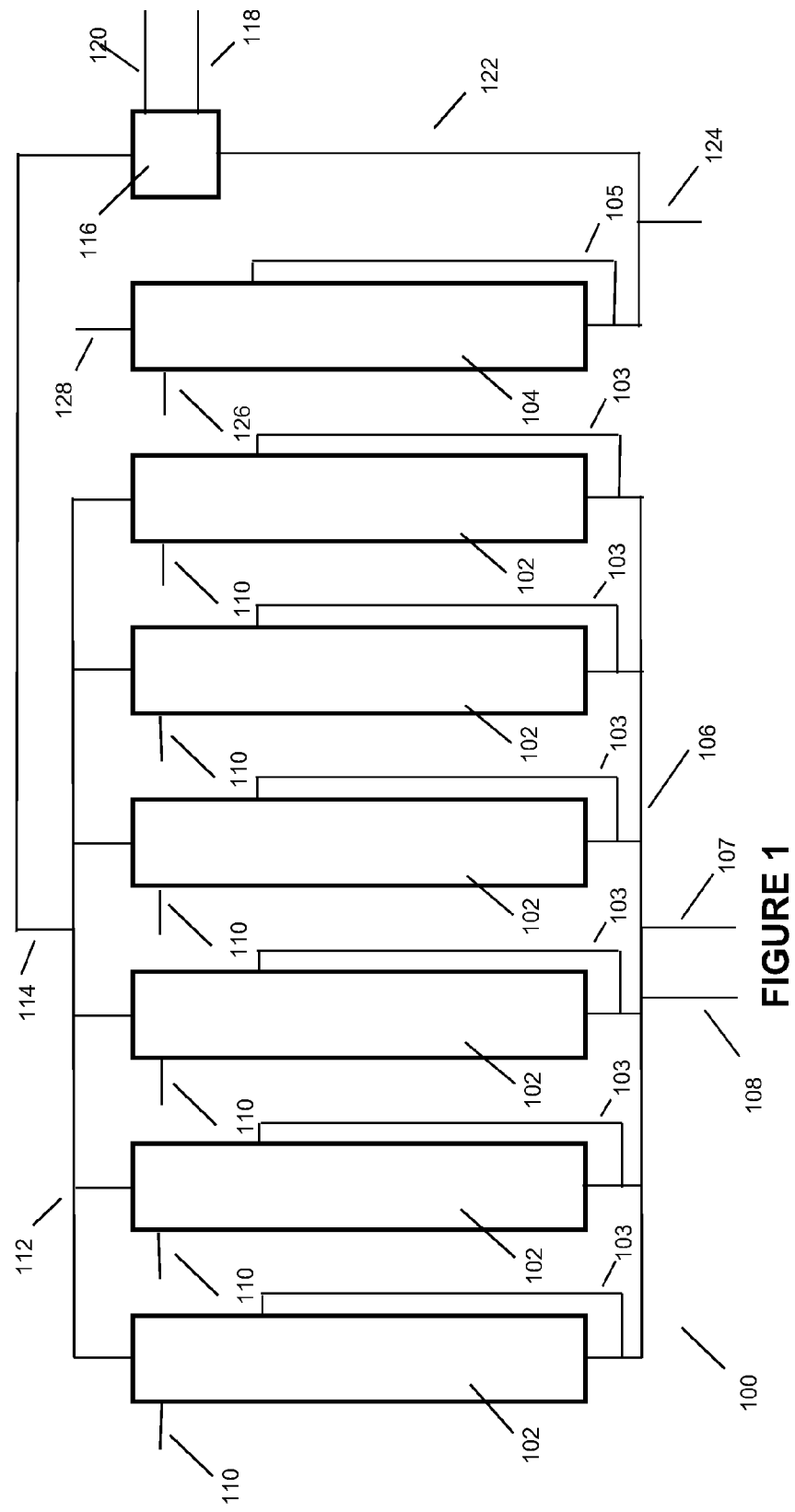
FIG. 1 is a schematic depiction of one type of fermentation system using the processes of this invention.

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the aqueous menstruum.

Carbon monoxide inhibition means that microorganisms are adversely affected by a high concentration of dissolved carbon monoxide in the aqueous menstruum resulting in a significantly reduced, e.g., reduced by at least 15 percent, conversion of carbon monoxide or hydrogen per gram of active cells per liter, all other conditions remaining the same. The inhibitory effect may occur in a localized region in the aqueous menstruum; however, the occurrence of a carbon monoxide inhibition is typically observed by assessing the specific activity rate, i.e., the mass bioconsumed per mass of active microorganism per unit time, which under steady-state conditions can be approximated by the overall conversion for the volume of aqueous menstruum in the reactor. The concentration of carbon monoxide dissolved in the aqueous menstruum that results in carbon monoxide inhibition varies depending upon the strain of microorganism and the fermentation conditions.

Aqueous menstruum means a liquid water phase which may contain dissolved compounds including, but not limited to hydrogen, carbon monoxide, and carbon dioxide.

The motive liquid may be any suitable liquid for introduction into the reactor. The motive liquid comprises sufficient amount of one or more of oxygenated organic compound and other surface active agent to enhance the formation of microbubbles.

Microbubbles are bubbles having a diameter of 500 microns or less.

The pressure at the point of injection into the aqueous menstruum is the sum of the absolute pressure at the point calculated as if the liquid head above such point were water. The partial pressure of a gas feed component is determined as the product of the mole fraction of a component in a gas mixture times the total pressure. The partial pressure of a component in the gas being fed to a reaction reactor is calculated as the mole fraction of that component times the pressure in the reaction reactor at the point of entry.

Stable gas-in-liquid dispersion means a mixture of gas bubbles in liquid where (i) the bubbles predominantly flow in the same direction as the liquid, and (ii) the dispersion is sufficiently stable that it exists throughout the aqueous menstruum, i.e., insufficient coalescing of bubbles occurs to destroy the dispersion.

Overview:

The processes of this invention use two deep, bubble column reactors in flow sequence that operate with certain gas feeds and operating parameters to achieve high conversions of carbon monoxide and hydrogen to oxygenated compound.

Substrate and Gas Feed:

Anaerobic fermentation to produce oxygenated organic compound uses a substrate comprising carbon monoxide, carbon dioxide and hydrogen, the later being for the hydrogen conversion pathway. The gas feed will typically contain nitrogen and methane in addition to carbon monoxide and hydrogen. Syngas is one source of a gas substrate. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas. Syngas is typically produced by a gasifier. Any of the aforementioned biomass sources are suitable for producing syngas. The syngas produced thereby will typically contain from 10 to 60 mole % CO, from 10 to 25 mole % $CO_2$ and from 10 to 60 mole % $H_2$. The syngas may also contain $N_2$ and $CH_4$ as well as trace components such as $H_2S$ and COS, $NH_3$ and HCN. Other sources of the gas substrate include gases generated during petroleum and petrochemical processing. These gases may have substantially different compositions than typical syngas, and may be essentially pure hydrogen or essentially pure carbon monoxide. The gas substrate may be obtained directly from gasification or from petroleum and petrochemical processing or may be obtained by blending two or more streams. Also, the gas substrate may be treated to remove or alter the composition including, but not limited to, removing components by chemical or physical sorption, membrane separation, and selective reaction. Components may be added to the gas substrate such as nitrogen or adjuvant gases such as ammonia and hydrogen sulfide.

For the sake of ease of reading, the term syngas will be used herein and will be intended to include gas substrates other than syngas.

Oxygenated Compounds and Microorganisms:

The oxygenated organic compound produced in the processes of this invention will depend upon the microorganism used for the fermentation and the conditions of the fermentation. Bioconversions of CO and $H_2/CO_2$ to acetic acid, n-butanol, butyric acid, ethanol and other products are well known. For example, a concise description of biochemical pathways and energetics of such bioconversions has been presented by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser.

No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 filed as U.S. Ser. No. 12/272,320 on Mar. 19, 2010. All of these references are incorporated herein in their entirety.

Aqueous Menstruum and Fermentation Conditions for Primary and Sequential Reactors:

The aqueous menstruum for both the primary and sequential reactors will comprise an aqueous suspension of microorganisms and various media supplements. The aqueous menstruum for the primary reactor may be substantially the same or may be different from the aqueous menstruum for the sequential reactor. The fermentation conditions for the primary and for the secondary reactors may be substantially the same or different.

The fermentation conditions in the primary reactor are preferably sufficient to effect between about 40 or 50 and 75 percent conversion of the carbon monoxide in gas feed. The fermentation conditions in the sequential reactor are preferably sufficient to convert at least about 40, preferably at least about 50, say, between about 50 and 75, percent of the total moles of hydrogen and carbon monoxide in its gas feed. The combined total molar conversion of carbon monoxide and hydrogen based upon net gas feed to both reactors (i.e., excluding gas feed to the sequential reactor from a primary reactor) is at least about 75, preferably at least about 80 or 85, percent. In some instances, the total molar conversion is in the range of about 85 to 95 percent of carbon monoxide and hydrogen in the net gas feed.

Suitable microorganisms generally live and grow under anaerobic conditions, meaning that dissolved oxygen is essentially absent from the fermentation liquid. Adjuvants to the aqueous menstruum may comprise buffering agents, trace metals, vitamins, salts etc. Adjustments in the menstruum may induce different conditions at different times such as growth and non-growth conditions which will affect the productivity of the microorganisms. Previously referenced U.S. Pat. No. 7,704,723 discloses the conditions and contents of suitable aqueous menstruum for bioconversion CO and $H_2/CO_2$ using anaerobic microorganisms.

The top of the deep, bubble column fermentation zones may be under pressure, at atmospheric pressure, or below ambient pressure. The menstruum is maintained under anaerobic fermentation conditions including a suitable temperature, say, between 25° and 60° C., frequently in the range of about 30° to 40° C. The conditions of fermentation, including the density of microorganisms, aqueous menstruum composition, and fermentation zone depth, are preferably sufficient to achieve the sought conversion efficiency of hydrogen and carbon monoxide.

The average residence time of the gas in the fermentation zone (average time for the bubble to move from the point of introduction to the upper surface of the menstruum) will depend upon not only the depth of the aqueous menstruum but also the size of the bubble when introduced and the internal fluid flows in the reactor. The average residence time of the gas in the reactor (average time for the bubble to move from the point of introduction to the upper surface of the menstruum) will depend upon not only the depth of the aqueous menstruum but also the size of the bubble when introduced and the internal fluid flows in the vessel defining the reactor. While baffles or other flow-directing devices can be used, they are not essential to this invention. The average residence time is preferably at least about 20 seconds, and most preferably at least about 30 seconds and may range up to 150 or 200 seconds or more.

Any suitable procedure may be used to start-up a deep, bubble column reactor. Typically, the reactor is filled with a gas not containing reactive oxygen. Although a wide variety of gases for blanketing can be used, such as gases containing carbon dioxide, nitrogen or lower alkane, e.g., alkane of 1 to 3 carbon atoms such as methane and natural gas, cost and availability considerations play a role in the selection of the blanketing gas as well as its acceptability to the anaerobic fermentation process and subsequent unit operations. The reactor is partially charged with aqueous menstruum containing microorganisms and gas feed is provided to grow the culture of microorganisms and additional aqueous menstruum is provided until the aqueous menstruum has obtained the desired height in the reactor and the density of microorganisms has reached its desired level. Start-up procedures for deep tank reactors are disclosed in co-pending U.S. patent application Ser. No. 13/243,159, filed on even date herewith and incorporated by reference in its entirety.

Deep, Bubble Column Reactors:

The deep, bubble column reactor can take any form that provides a substantial depth of aqueous menstruum. The deep reactor is of a sufficient volume that the fermentation process is commercially viable. Preferably the primary deep reactors are designed to contain at least 1 million, and more preferable at least about 5, say about 5 to 25 million, liters of aqueous menstruum. These reactors are characterized as having a height of at least about 10, often between about 10 or 15 and 30, meters and an aspect ratio of height to diameter of at least about 0.5:1, say, 0.5:1 to 5:1, preferably between about 0.75:1 to 3:1. Often commercial-scale reactors are characterized by a width of at least about 5, preferably at least about 7, say, between about 7 and 30, meters. While the reactors are typically circular in cross-section, other cross-sectional configurations can be used provided that uniformity in the liquid phase is obtained. The depth of the aqueous menstruum under steady state production conditions will occupy nearly the full height of the reactor. The height of the aqueous menstruum will establish a hydrostatic pressure gradient along the axis of the reactor.

The deep, bubble column reactors may contain axial-flow promoting devices such as baffles, down draft tubes and the like although these devices add to the capital costs of the reactors. Hence, most bubble column reactors do not contain these devices.

The depth of the aqueous menstruum in a bubble column reactor will occupy either the full height or nearly the full height of the deep, bubble column reactor. The height of the aqueous menstruum will establish a hydrostatic pressure gradient along the reactor. The dispersion of gas and liquid in the dispersion stream must overcome this hydrostatic pressure at the point where it enters the reactor. Thus if the gas substrate enters at a point of 10 meters below the liquid surface the static pressure head inside the vessel would equal approximately 100 kPa gauge and for a liquid height of 15 meters the static pressure head would equal approximately 150 kPa gauge.

Gas Feed Supply and Injection

The gas feed to the primary reactor contains carbon monoxide, carbon dioxide, hydrogen, and nitrogen and may contain other components as discussed above. Gas feed includes fresh syngas or other substrate gas and may, if desired, contain recycled off-gas from that primary reactor or from another reactor and any other gas fed to the reactor for any purpose, including but not limited to gaseous adjuvants and diluents. The gas feed for a sequential reactor comprises off-gas from at least one primary reactor and may, if desired, contain fresh syngas or other substrate gas or contain recycled off-gas from that reactor.

The rate of supply of the gas feed under steady state conditions to each of the primary and sequential reactors is such that the rate of transfer of carbon monoxide and hydrogen to the liquid phase matches the rate that carbon monoxide and hydrogen are bioconverted. Hence, the dissolved concentration of carbon monoxide and hydrogen in the aqueous phase remains constant, i.e., does not build-up. The rate at which carbon monoxide and hydrogen can be consumed will be affected by the nature of the microorganism, the concentration of the microorganism in the aqueous menstruum and the fermentation conditions. As the rate of transfer of carbon monoxide and hydrogen to the aqueous menstruum is a parameter for operation, conditions affecting the rate of transfer such as interfacial surface area between the gas and liquid phases and driving forces are important. For instance, at a given flow rate of gas feed having a given composition to a reactor, the rate of transfer of carbon monoxide and hydrogen can vary widely depending upon the size of the microbubbles and upon the pressure. As discussed below, the processes of this invention supply gas feed by injection using a motive fluid. Variations in the motive liquid flow rate can be used to modulate the microbubble size and thus modulate the rate of transfer of carbon monoxide and hydrogen to the liquid phase.

The processes of this invention use at least one injector using a motive fluid for supplying gas feed to the aqueous menstruum. Preferably the reactor contains 2 or more injectors, and commercial scale reactors will often contain at least 2, often 4 to 8 or 10, laterals of injectors with as many as 100 or more injectors. The number of injectors used is typically selected based upon the ability to be able to transfer adequate amounts of gas substrate under steady-state operating conditions and to enhance cross-sectional uniformity of the gas phase in the reactor.

The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The large cross-sectional dimension of the injectors provides several benefits in addition to being able to produce microbubbles. First, they are not prone to fouling including where aqueous menstruum is used as the motive liquid as would be a sparger designed to produce microbubbles. Second, where the aqueous menstruum is used as the motive fluid, high momentum impact of the microorganisms with solid surfaces is minimized thereby minimizing the risk of damage to the microorganisms. Third, the energy required to provide microbubbles of a given size is often less than that required to form microbubbles of that size using a microbubble sparger. Fourth, a high turn down ratio can be achieved. And fifth, the microbubble size can be easily varied over a wide range.

The bubble size generated by the injectors will be influenced by, among other factors, the rate of liquid flow through the injector and the ratio of gas phase to liquid phase passing through the injector as well as characteristics of the aqueous menstruum itself including, but not limited to its static liquid depth. Consequently, an injector can be operated to provide a selected bubble size which enhances the ability to use the injector in a modulation mode, i.e., provide the adjustment in the rate of transfer of carbon monoxide to the liquid phase based upon the size of the culture and its ability of the culture to bioconvert the carbon monoxide. The modulation can also be used to obtain, if desired, a stable gas-in liquid dispersion. The modulation can be obtained by changing one or more of (i) the gas to liquid flow ratio to the injector thus changing the volume of gas feed and (ii) changing the rate of motive liquid and thus the bubble size which affects the rate of transfer of carbon monoxide from the gas phase to liquid phase. Additionally, modulation can be obtained by changing the gas feed composition and thus the mole fraction of carbon monoxide in the gas feed.

Preferably the gas feed is introduced by the injector into the menstruum in the form of microbubbles having diameters in the range of 0.01 to 0.5, preferably 0.02 to 0.3 millimeter. At start-up and where desired for enhancing mixing, larger bubble sizes, in the range of 100 to 5000 microns in diameter may be used. Also a portion of the gas feed may be introduced by sparging to generate large bubbles, say, 1 to 5 or 10, millimeters in diameter, for assisting in mixing the aqueous menstruum. The gas substrate may be introduced into the bottom portion of the deep, bubble column reactor as a gas stream or as a gas in liquid dispersion as disclosed in U.S. patent application Ser. No. 12/826,991, filed Jun. 30, 2010. The presence of the oxygenated organic compound and/or other surface active agent enhances the formation of fine microbubbles.

The motive liquid may be any suitable liquid for introduction into the reactor. Advantageously, the motive liquid is one or more of aqueous menstruum, liquid derived from aqueous menstruum or make-up liquid to replace aqueous menstruum withdrawn from product recovery. Preferably the motive liquid comprises aqueous menstruum.

The flow rate of motive liquid used in an injector will depend upon the type, size and configuration of the injector and the sought bubble size of the gas feed. In general, the velocity of the dispersion stream leaving the injector is frequently in the range of 0.5 to 5 meters per second and the ratio of gas to motive liquid is in the range of from about 1:1 to 3:1 actual cubic meters per cubic meter of motive liquid.

Often the microbubbles form a stable gas-in-water dispersion. The introduction of the microbubbles into the aqueous menstruum places the microbubbles in a dynamic environment. The height of the aqueous menstruum means that microbubbles in the dispersion will experience different static pressure heads as they travel upwardly through the reactor. Increased pressure will, all else substantially the same, reduce the size of a microbubble. For a given gas feed rate, a greater surface area will be provided by the smaller microbubbles which enhances mass transfer. The size of a microbubble will also be affected by the diffusion of gases from the microbubble to the liquid phase. As carbon monoxide and hydrogen constitute a significant mole fraction of the microbubble as it is introduced into the aqueous menstruum, the dynamic conditions will promote a population of microbubbles that have small diameters to aid in maintaining the gas-in-water dispersion throughout the reactor.

Product Recovery for Primary and Sequential Reactors:

The bubbles in the fermentation vessel move upwardly through the aqueous menstruum and are removed in an upper portion of the vessel. The fermentation vessel may have added from time to time or continuously one or more streams of water, nutrients or adjuvants, and microorganisms. A portion of the aqueous menstruum is withdrawn from time to time or continuously from the reactor for product recovery. Usually, the withdrawal is made at a point at the upper portion of the aqueous menstruum in the vessel. Product recovery can consist of known equipment arrangements for removal of residual cell material, separation and recovery of liquid products from the fermentation liquid, return of recovered fermentation liquid and purging of waste streams and materials. Suitable equipment arrangement can include filters, distillation columns, membrane systems and other separation equipment. US 2009/0215139 A1 shows an arrangement for a product recovery reactor that recovers an ethanol product from a bioreactor, herein incorporated by reference in its entirely.

Carbon Dioxide Removal:

Preferably carbon dioxide is removed from at least one of the aqueous menstruum in a primary reactor or, preferably, from the off-gas from a primary reactor. Any suitable carbon dioxide removal process may be used including amine extraction, alkaline salt extractions, water absorption, membrane separation, adsorptions/desorption, and physical absorption in organic solvents. Considerable flexibility exists in the carbon dioxide removal step in that certain amounts of carbon dioxide are to be fed to the sequential reactor. In preferred aspects of the invention, the off-gas will contain at least about 15, say, between 15 and 50, mole percent of total hydrogen and carbon monoxide. Preferably the carbon dioxide concentration in the off-gas is between about 2 and 40, more preferably between about 5 or 10 and 20, mole percent. The off-gas may contain at least about 15, and often about 20 to 50, mole percent nitrogen.

A preferred process for removal of carbon dioxide from gases is by contacting the gas with an aqueous solution containing oxygenated organic compound. This process for removing carbon dioxide from gas to be fed to a reactor, including between sequential fermentation stages, is disclosed in U.S. Patent application No. 2008/0305539, filed Jul. 23, 2007, herein incorporated by reference in its entirety. See also, U.S. patent application Ser. No. 12/826,991, filed Jun. 30, 2010 herein incorporated by reference in its entirety, which discloses contacting a gas stream with a mixture of water and a surface active agent under pressure to sorb carbon dioxide and phase separating the gas and liquid stream to provide a gas stream with reduced carbon dioxide concentration to be used a feed to a reactor. United States published patent application 2008/0305539 A1 discloses the use of membranes to remove carbon dioxide from a membrane supported fermentation system to prevent dilution of concentrations of carbon monoxide and hydrogen in a multistage system.

If desired, a portion of the carbon dioxide dissolved in the liquid phase of the aqueous menstruum can be removed. Any convenient unit operation for carbon dioxide removal can be used, but the preferred operation is separation by reducing the pressure to atmospheric or lower pressure to flash carbon dioxide gas from the liquid phase.

Feed Gas to Sequential Reactor:

The gas feed to the sequential reactor contains off-gas, which may or may not have been treated to remove carbon dioxide, and may contain gas from other sources. Preferably at least about 90 volume percent, and most preferably essentially all, of the off-gas from a primary reactor is passed to a sequential reactor as at least a portion of the gas feed. A portion of the gas feed to a sequential reactor may be its recycled off-gas, especially if the ratio of carbon monoxide conversion to hydrogen conversion in the sequential reactor is less than that of a primary reactor. Also, fresh gas feed such as provided to the primary reactor may be used. Preferably at least about 50 volume percent, and often between 70 and 100, volume percent of the feed gas to the sequential reactor is from off-gases from primary reactors.

Generally a primary reactor will result in most of the conversion of carbon monoxide and a large portion of the conversion of hydrogen in the fermentation system. Consequently the use of more than one primary reactor providing off-gas to a sequential reactor may be desired. The ratio will depend upon the extent of conversion of substrate in the primary reactors and the relative volume of the sequential reactor. Often the ratio is from 2:1 to 7:1 or 8:1 for primary and sequential reactors of the same volume.

As the gas feed to the sequential reactor will contain off-gas from a primary reactor, inert gas such as nitrogen and methane and carbon dioxide, to the extent not removed, will be in a higher mole ratio to total carbon monoxide and hydrogen than in the gas feed to the primary reactor. Additionally, the mole ratio of carbon monoxide to hydrogen in the gas feed to the sequential reactor will often be lower than that ratio in the gas feed to the primary reactor due to preferential conversion of carbon monoxide in the primary reactor. Thus the partial pressure of carbon monoxide in the gas feed where introduced into the sequential reactor can be maintained below that which would be deleterious to the microorganisms.

The gas feed to the sequential reactor contains carbon monoxide, hydrogen, carbon dioxide and nitrogen. The mole concentration of carbon dioxide in the gas feed to the sequential reactor is often less than about 60, preferably less than about 40, mole percent of that in the off-gas from the primary reactor. Often carbon dioxide comprises from about 2 to 40, preferably between about 5 or 10 and 20, mole percent of the gas feed. The concentration of nitrogen in the gas feed to the sequential reactor is frequently at least about 5 or 10, preferably in the range of about 15 to 50 (if no fresh gas feed is added), mole percent. The mole ratio of carbon dioxide to nitrogen is typically between about 0.5:1 to 5:1. The gas feed preferably contains at least about 5, more preferably at least about 10, say, about 10 to 40, mole percent carbon monoxide and preferably at least about 10, say, about 10 to 60, mole percent hydrogen.

Additional Flow Series Fermentation Reactors:

As stated above, the off-gas from a sequential reactor may be subjected to further fermentation to convert carbon monoxide and hydrogen to oxygenated compound. Due to the conversion of carbon monoxide and hydrogen in the sequential reactor, even with removal of most of the carbon dioxide, the mole ratio of inerts such as nitrogen to total carbon monoxide and hydrogen in the off-gas will be significantly greater than that in the gas feed to the sequential reactor. However, the mass of off-gas from the sequential reactor will be considerably less than the mass of the gas feed to the sequential reactor. Hence, unless significant amendment of the off-gas with, e.g., fresh gas substrate, is made, the fermentation reactor volume required for additional conversion is substantially lower than that required for the sequential reactor. Thus, flexibility exists in the type of reactor used, with a practical limitation that the capital and operating costs for the additional flow series reactor are off set by the incremental production. Suitable reactors include, but are not limited to, deep bubble column reactors, stirred tank reactors, and pipe reactors, especially baffled pipe reactors.

DRAWINGS

A general understanding of the invention and its application may be facilitated by reference to FIG. 1. FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to making other oxygenated products such as acetic acid, butanol, propanol and acetone.

Apparatus 100 has a plurality of primary deep, bubble column fermentation vessels 102. Six are shown, although greater or fewer vessels can be used, and secondary deep, bubble column fermentation vessel 104. In some instances, the conversion of gas substrate in the primary vessels and the volume of off-gas and hydrogen and carbon monoxide concentration in the off-gas from three to seven primary vessels are suitable for producing the volume of gas feed needed for one sequential vessel of a similar size. This provides the advantage of being able to switch functions of a vessel, i.e., the piping to a primary vessel 102 may be changed to make the vessel serve as a sequential vessel 104, and the piping to a sequential vessel 104 may be changed to make the vessel serve as a primary vessel 102. A vessel can be taken off line for servicing without the necessity to shut down the apparatus, and the fermentation in the vessels can be started up individually. Of course, the number and size of the primary vessels can vary as desired.

Gas feed is supplied via line 107 to flow distribution network 106. As shown, make-up water and other additives can be supplied to flow distribution network 106 via line 108. Flow distribution network is in communication with injectors, preferably slot injectors, located in the bottom portion of each primary vessel 102. Motive liquid for the injectors is aqueous menstruum withdrawn from each primary vessel via line 103 and passed to flow distribution network 106.

Each of the primary vessels contains aqueous menstruum including microorganisms for the production of ethanol. As shown, liquid is withdrawn via line 110 from a top portion of each of the primary vessels 102 and processed to recover oxygenated organic compound. Off-gas is withdrawn into off-gas header system 112 from the top of each of the primary vessels 102. The off-gas is passed via line 114 to carbon dioxide removal device 116. Carbon dioxide removal device may be any suitable device. As shown, carbon dioxide is removed by sorption into an aqueous stream containing ethanol. The sorbent is provided via line 118 and spent sorbent is withdrawn from carbon dioxide removal device 116 via line 120 for regeneration. A treated off-gas is produced in carbon dioxide removal device 116 and is withdrawn via line 122 and passed to an injector at a bottom portion of sequential vessel 104. As shown, liquid make-up with any needed adjuvants from line 124 is admixed with the treated off-gas. Motive liquid for the injector is aqueous menstruum withdrawn from sequential vessel 104 and passed to the injectors via line 105.

Sequential vessel 104 contains aqueous menstruum including microorganisms for the production of ethanol. As shown, liquid is withdrawn via line 126 from a top portion of the sequential vessel 104 and processed to recover oxygenated organic compound. Off-gas is withdrawn via line 128 from sequential vessel 104. This off-gas may be used in a further sequential vessel for the production of additional ethanol or may be directed for other use such as combustion to generate process heat.

Figure 2:
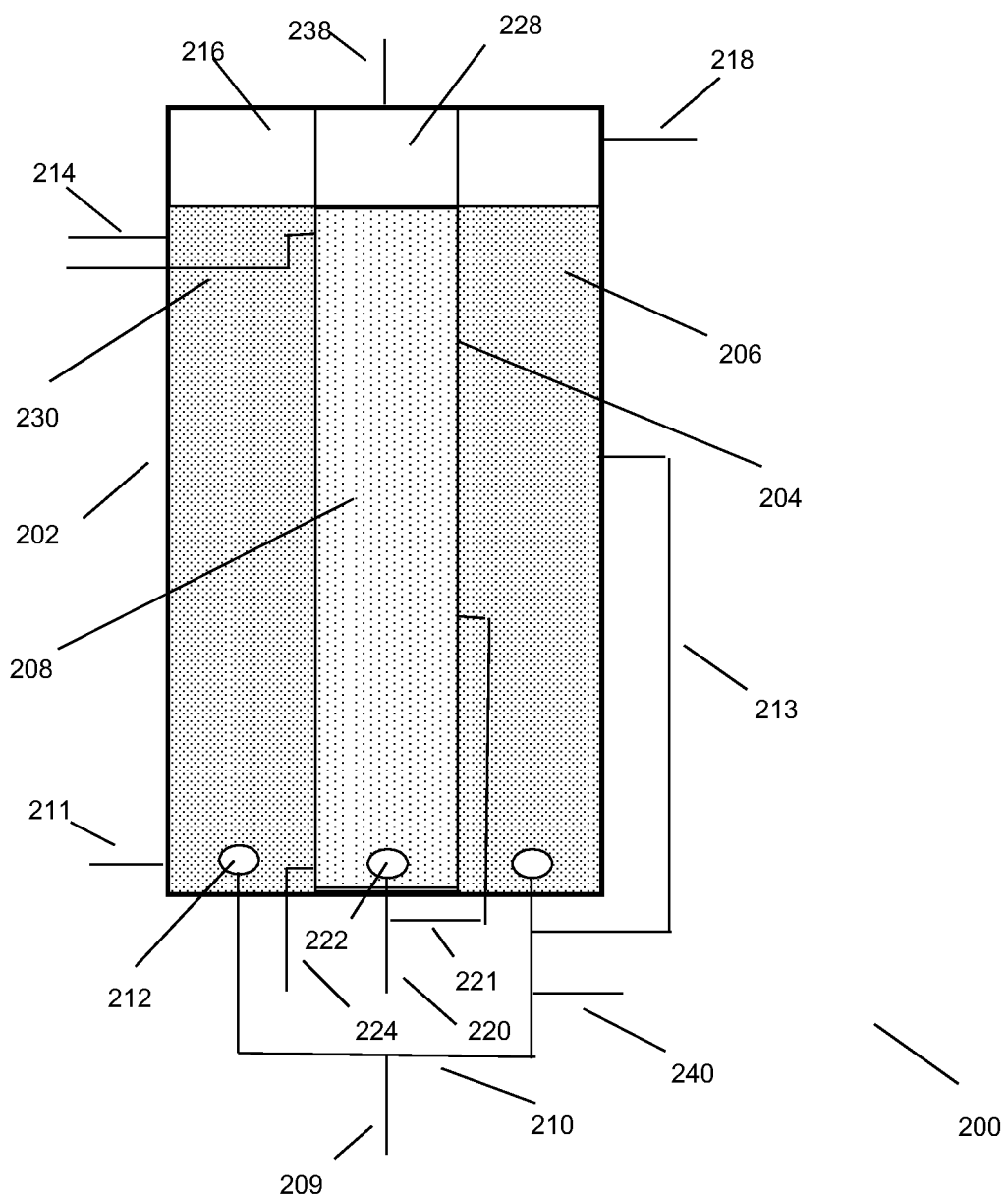
FIG. 2 is a schematic depiction of an integrated deep, bubble reactor and a sequential reactor.

FIG. 2 is a schematic depiction of an integrated primary and secondary deep, bubble column fermentation vessel generally designated as 200. Primary deep, bubble column fermentation vessel 202 has located therein sequential deep, bubble column fermentation vessel 204. As depicted the sequential vessel 204 is annularly positioned in cylindrical primary vessel 202. The primary vessel 202 contains aqueous menstruum 206 and the sequential vessel contains aqueous menstruum 208. Fresh gas substrate is passed via line 209 to flow distribution network 210 which is in fluid communication with injector laterals 212 having a plurality of slot injectors located at the bottom portion of primary vessel 202. Motive liquid for the injectors is aqueous menstruum withdrawn from vessel 202 via line 213 and passed to flow distribution network 210. Make-up water and adjuvants can be provided to the bottom portion of primary vessel 202 via line 211. The gas bubbles pass upwardly through aqueous menstruum 206 wherein ethanol is produced. At a top portion of the aqueous menstruum, line 214 withdraws liquid for product recovery. The off-gas leaving aqueous menstruum 206 collects at the top plenum 216 of primary vessel 202 and is removed via line 218 for carbon dioxide removal as depicted in FIG. 1.

After carbon dioxide removal, off-gas from the primary vessel is passed to flow distribution network 220 which is in fluid communication with injector lateral 222 located at the bottom portion of sequential vessel 204. Motive liquid for the injectors is aqueous menstruum withdrawn from vessel 204 via line 221 and passed to flow distribution network 220. A portion of the aqueous menstruum 208 is withdrawn via line 230 at a top portion of sequential vessel 204 for ethanol recovery. The off-gas from aqueous menstruum 208 is collected in plenum 228 and is removed via line 238.

Figure 3:
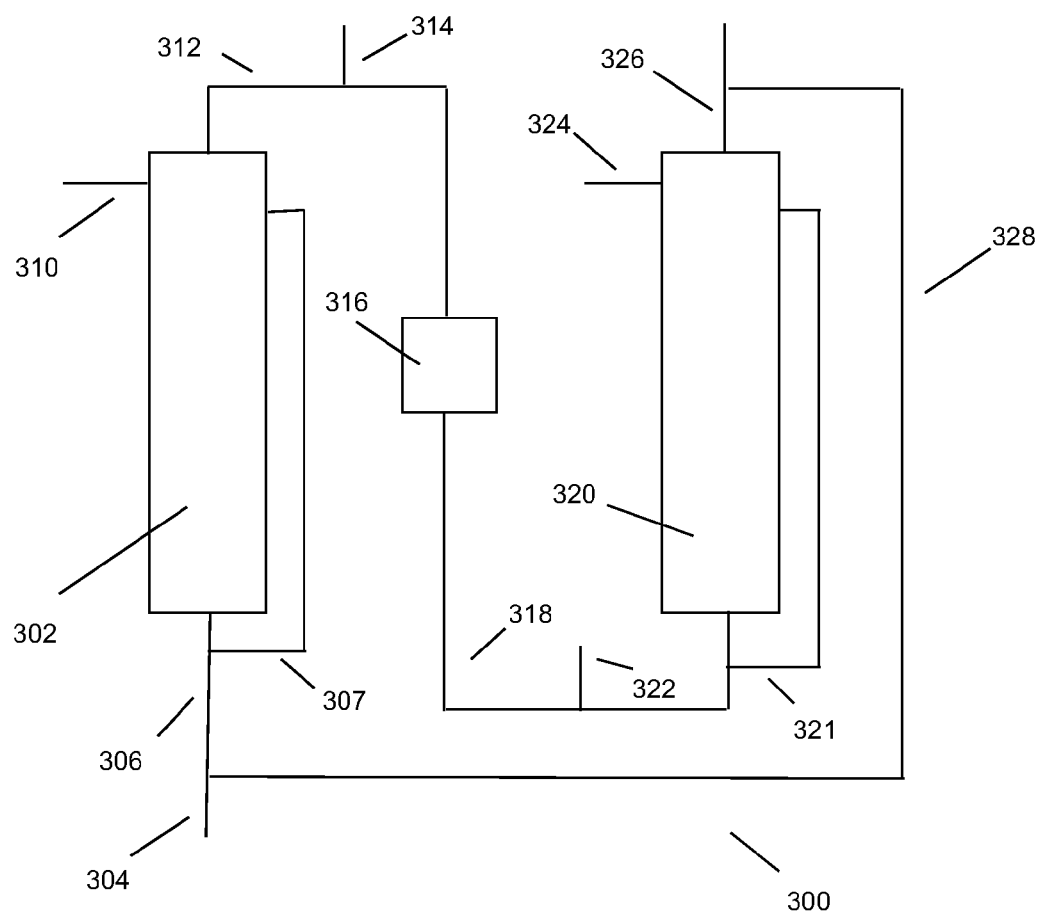
FIG. 3 is a schematic depiction of a fermentation system in which a sequential reactor provides off-gas for reducing the carbon monoxide mole fraction in the gas feed to a primary deep, bubble column reactor.

FIG. 3 is a schematic depiction of an apparatus generally designated as 300 suitable for practicing the processes of this invention in which a portion of the off-gas from the sequential reactor is recycled to the primary reactor. FIG. 3 omits minor equipment such as pumps, compressors, valves, instruments and other devices the placement of which and operation thereof are well known to those practiced in chemical engineering. FIG. 3 also omits ancillary unit operations. The process and operation of FIG. 3 will be described in the context of the recovery and production of ethanol. The process is readily adaptable to making other oxygenated products such as acetic acid, butanol, isopropanol and acetone.

Apparatus 300 has a plurality of primary deep, bubble column fermentation vessels 302, only one of which is shown. Feed gas is supplied by line 304 to flow distribution network 306 which is in communication with slot injectors located in a bottom portion of primary vessel 302. Primary vessel 302 contains aqueous menstruum including microorganisms for the production of ethanol. Motive liquid for the injectors is aqueous menstruum withdrawn from vessel 302 via line 307 and passed to flow distribution network 306.

As shown, liquid is withdrawn via line 310 from a top portion of primary vessel 302 and processed to recover oxygenated organic compound. Off-gas is withdrawn into off-gas header system 312 from the top of the primary vessel 302. A gas purge may be taken at line 314 and passed to gas clean up operations. The off-gas is passed to carbon dioxide removal device 316. Carbon dioxide removal device may be any suitable device. Off-gas is withdrawn from carbon dioxide removal device 316 and passed to flow distribution network 318 which is in fluid communication with slot injectors in sequential vessel 320. As shown, liquid make-up with any needed adjuvants is produced in carbon dioxide removal device 316 and can be provided to flow distribution network 318 via line 322. Sequential vessel 320 contains aqueous menstruum including microorganisms for the production of ethanol. Motive liquid for the injectors is aqueous menstruum withdrawn from vessel 320 via line 321 and passed to flow distribution network 318.

As shown, liquid is withdrawn via line 324 from a top portion of the sequential vessel 320 and processed to recover oxygenated organic compound. Off-gas is withdrawn via line 326 from sequential vessel 320. This off-gas may be used in a further sequential vessel for the production of additional ethanol or may be directed for other use such as combustion to generate process heat. The apparatus depicted in FIG. 3 is adapted to supply via line 328 a portion of the off-gas from sequential vessel 320 to flow distribution network 306 for supply to primary vessel 302. Thus a portion of the nitrogen can be returned to primary vessel 302.

What is claimed is:

1. A process for the bioconversion of a gas feed containing gas substrate comprising carbon monoxide, carbon dioxide and hydrogen in an aqueous menstruum containing microorganisms suitable for converting said gas substrate to oxygenated organic compound comprising:
   a. providing the aqueous menstruum in at least one primary deep, bubble column reactor to a height of at least 10 meters wherein the gas feed is injected in a bottom portion of the reactor and wherein the pressure of the aqueous menstruum is at least about 100 kPa gauge at said portion,
   b. continuously supplying as microbubbles said gas feed by injection using a motive liquid to the bottom portion of said reactor, said gas feed:
      (i) containing at least about 2 mole percent nitrogen,
      (ii) containing at least about 5 mole percent carbon dioxide,
      (iii) having a mole ratio of hydrogen to carbon monoxide between about 1:6 to 6:1, and
      (iv) having mole fractions of carbon dioxide and nitrogen sufficient to provide a carbon monoxide partial pressure at the point of injection of less than about 80 kPa;
   c. converting less than about 80 percent of the carbon monoxide in the gas feed supplied to the primary deep, bubble column reactor to oxygenated organic compound and providing an off-gas above the aqueous menstruum;
   d. optionally removing at least a portion of the carbon dioxide from the aqueous menstruum in the primary deep, bubble column reactor or from at least a portion of the off-gas from the primary deep, bubble column reactor;
   e. continuously supplying as microbubbles at least a portion of the off-gas by injection using a motive liquid to a lower portion of at least one sequential deep, bubble column reactor containing aqueous menstruum in which said off-gas passes upwardly through the aqueous menstruum wherein the off-gas has a mole fraction of nitrogen sufficient to avoid a mass transfer of carbon monoxide to the aqueous menstruum that results in carbon monoxide inhibition; and
   f. converting sufficient hydrogen and carbon monoxide in the off-gas to oxygenated organic compound such that at least about 75 percent of the total moles of carbon monoxide and hydrogen in the gas feed to the primary deep, bubble column reactor is converted to oxygenated compound.

2. The process of claim 1 wherein the oxygenated compound comprises at least one of acetic acid and ethanol.

3. The process of claim 2 wherein the gas feed to the primary deep, bubble column reactor has a mole ratio of hydrogen to carbon monoxide between about 1:4 to 2:1.

4. The process of claim 2 wherein the mole ratio of nitrogen to carbon dioxide in the gas substrate is within the range of 0.2:1 to 2:1.

5. The process of claim 4 wherein the carbon monoxide partial pressure at the location where the gas substrate enters the primary deep, bubble column reactor is between about 20 and 75 kPa.

6. The process of claim 1 wherein in step (c) about 60 to 75 percent of the carbon monoxide in the gas feed supplied to the primary deep, bubble column reactor is converted to oxygenated organic compound.

7. The process of claim 1 wherein at least a portion of the carbon dioxide is removed from at least one of the aqueous menstruum in the primary, deep, bubble column reactor and the off-gas from the primary, deep, bubble column reactor.

8. The process of claim 1 wherein the pressure at the location where the gas feed enters the deep, bubble column reactor is at a pressure in the range of about 150 to 300 kPa gauge.

9. The process of claim 1 wherein the gas feed to the sequential reactor contains between 15 and 50 mole percent of total hydrogen and carbon monoxide, between about 5 and 35 mole percent carbon dioxide and between about 15 to 50, mole percent nitrogen.

10. The process of claim 1 wherein gas substrate is fed to more than one primary deep, bubble column reactor and the off-gas from each is combined and treated to remove at least a portion of the carbon dioxide to provide a combined treated off-gas and the combined treated off-gas is fed to one or more sequential reactors.

11. The process of claim 1 wherein at least about 90 percent (excluding any carbon dioxide removed) of the off-gas from the primary deep, bubble column reactor is supplied to the sequential deep, bubble column reactor.

12. The process of claim 1 wherein changing the size of the microbubbles is used to modulate the transfer of carbon monoxide to the aqueous menstruum in the primary deep, bubble column reactor.

13. The process of claim 12 wherein the injection is by a slot injector and the motive liquid comprises aqueous menstruum.

14. The process of claim 13 wherein the size of the microbubbles is changed to modulate the transfer of carbon monoxide to the aqueous menstruum in the sequential deep, bubble column reactor.

15. The process of claim 14 wherein the injection is by a slot injector and the motive liquid comprises aqueous menstruum.

16. The process of claim 1 wherein each of the primary deep, bubble column reactor and the sequential deep, bubble column reactor have a height of aqueous menstruum therein of between about 15 and 30 meters.

17. The process of claim 16 wherein the primary deep, bubble column reactor has a capacity of between about 5 and 25 million liters.

18. The process of claim 16 wherein more than one primary deep, bubble column reactors are used and the primary deep, bubble column reactor and the sequential deep, bubble column reactor.

19. A process for the bioconversion of a gas feed containing gas substrate comprising carbon monoxide, carbon dioxide and hydrogen in an aqueous menstruum containing microorganisms suitable for converting said gas substrate to oxygenated organic compound comprising at least one of ethanol and acetic acid or salts thereof comprising:
   a. providing the aqueous menstruum in at least one primary deep, bubble column reactor to a height of at least 15 meters wherein the gas feed is injected in a bottom portion of the reactor,
   b. continuously supplying said gas feed by injection using a motive liquid comprising aqueous menstruum to the bottom portion of said reactor to form microbubbles in the range of between about 20 and 300 microns, said gas feed:
      (i) containing at least about 2 mole percent nitrogen,
      (ii) containing at least about 5 mole percent carbon dioxide,
      (iii) having a mole ratio of hydrogen to carbon monoxide between about 1:2 to 2:1, and
      (iv) having mole fractions of carbon dioxide and nitrogen sufficient to provide a carbon monoxide partial pressure at the point of injection of between 20 and 75 kPa;
   c. converting between about 60 and 75 percent of the carbon monoxide in the gas feed supplied to the primary deep, bubble column reactor to oxygenated organic compound and providing an off-gas above the aqueous menstruum, wherein the rate of flow of the motive liquid provides microbubbles of the gas feed of a size sufficient to provide a rate of transfer of carbon monoxide to the aqueous menstruum to achieve the about 60 to 75 percent conversion of carbon monoxide in the gas feed without building-up the concentration of dissolved carbon monoxide in the aqueous menstruum;
   d. continuously supplying a gas feed containing at least a portion of the off-gas from the primary deep, bubble column reactor to a lower portion of at least one sequential deep, bubble column reactor containing aqueous menstruum in which said off-gas passes upwardly through the aqueous menstruum wherein (i) the gas feed is supplied by injection using a motive liquid comprising aqueous menstruum to provide microbubbles of the gas feed and (ii) the off-gas has a mole fraction of nitrogen sufficient to avoid a mass transfer of carbon monoxide to the aqueous menstruum that results in carbon monoxide inhibition; and
   e. converting sufficient hydrogen and carbon monoxide in the off-gas to oxygenated organic compound in the sequential deep, bubble column reactor such that at least about 80 percent of the total moles of carbon monoxide and hydrogen in the gas feed to the primary deep, bubble column reactor is converted to oxygenated compound.

20. The process of claim 19 wherein at least a portion of the carbon dioxide is removed from the aqueous menstruum in the primary deep, bubble column reactor or from at least a portion of the off-gas from the primary deep, bubble column reactor.

* * * * *